United States Patent [19]

Schaart et al.

[11] Patent Number: 5,254,782
[45] Date of Patent: Oct. 19, 1993

[54] CONTINUOUS PROCESS FOR THE TELOMERIZATION OF CONJUGATED DIENES

[75] Inventors: Barend J. Schaart; Hendrik L. Pelt, both of Terneuzen; Grant B. Jacobsen, Hoek, all of Netherlands

[73] Assignee: The Dow Chemical Company, Midland, Mich.

[21] Appl. No.: 768,541

[22] PCT Filed: Dec. 21, 1990

[86] PCT No.: PCT/EP90/02263

§ 371 Date: Aug. 16, 1991

§ 102(e) Date: Aug. 16, 1991

[30] Foreign Application Priority Data

Dec. 29, 1989 [NL] Netherlands ............... 8903182

[51] Int. Cl.$^5$ .................................................. C07C 2/18
[52] U.S. Cl. ....................................... 585/509; 568/675; 568/690
[58] Field of Search .............. 585/509, 514; 568/840

[56] References Cited

U.S. PATENT DOCUMENTS

| | | |
|---|---|---|
| 3,499,042 | 3/1970 | Smutny . |
| 3,518,315 | 6/1970 | Smutny . |
| 3,530,187 | 9/1970 | Shryne . |
| 3,670,032 | 6/1972 | Romanelli . |
| 3,676,470 | 7/1972 | Takahashi et al. . |
| 3,746,749 | 7/1973 | Mitsuyasu et al. . |
| 4,142,060 | 2/1979 | Kuntz ................... 502/162 |
| 4,146,738 | 3/1979 | Jadamus et al. . |
| 4,196,135 | 4/1980 | Enomoto et al. . |
| 4,356,333 | 10/1982 | Yoshimura et al. . |
| 4,377,719 | 3/1983 | Pittman, Jr. et al. ............ 585/509 |
| 4,417,079 | 11/1983 | Yoshimura et al. . |
| 4,620,048 | 10/1986 | Ver Strate et al. .................. 585/10 |
| 4,687,876 | 8/1987 | Nozaki ............. 585/509 |
| 4,824,817 | 4/1989 | Drent ................ 502/154 |
| 4,992,609 | 2/1991 | Maeda et al. ............... 585/509 |
| 5,100,854 | 3/1992 | Maeda et al. ............... 502/164 |

FOREIGN PATENT DOCUMENTS

| | | |
|---|---|---|
| 0218100 | 4/1987 | European Pat. Off. . |
| 9013531 | 11/1990 | PCT Int'l Appl. . |
| 1178812 | 1/1970 | United Kingdom . |
| 1248592 | 10/1971 | United Kingdom . |
| 1248593 | 10/1971 | United Kingdom . |
| 1256357 | 12/1971 | United Kingdom . |
| 1326454 | 8/1973 | United Kingdom . |
| 1354507 | 5/1974 | United Kingdom . |
| 2114974 | 9/1983 | United Kingdom . |

OTHER PUBLICATIONS

A. Behr, "Homogeneous Transition Metal Catalysts", Aspects of Homogeneous Catalysis (1984), vol. 5, pp. 3-73.

Primary Examiner—Anthony McFarlane

[57] ABSTRACT

Continuous process for the telomerization of conjugated dienes comprising reacting a conjugated diene with a compound containing an active hydrogen atom in the liquid phase in the presence of a Group VIII transition metal catalyst, a ligand compound of a tertiary phosphorous, arsenic or antimony, and a catalyst promoter compound having basic properties.

17 Claims, No Drawings

CONTINUOUS PROCESS FOR THE TELOMERIZATION OF CONJUGATED DIENES

The present invention relates to a continuous process for the telomerization of conjugated dienes comprising reacting a conjugated diene with a compound containing an active hydrogen atom in the liquid phase in the presence of a Group VIII transition metal catalyst and a tertiary phosphorous, arsenic or antimony ligand compound.

The telomerization reaction, which has been known per se for many years, involves the oligomerization and especially the dimerization of a conjugated diene under the concomitant addition of a nucleophilic agent, for example a compound containing an active hydrogen atom. The nucleophile is introduced mainly at the terminal position of the oligomer and especially of the dimer of the conjugated diene.

Telomerization reactions catalyzed by Group VIII transition metal catalysts are described extensively in the prior art. In the late sixties and early seventies attention was primarily focussed on the optimization of conversion and selectivity of the telomerization reaction under batch conditions. Representative publications are U.S. Pat. No. 3,499,042, U.S. Pat. No. 3,518,315, U.S. Pat. No. 3,530,187, GB-A 1178812, FR-A 1583249, NL-A 6816008, GB-A 1248593, NL-A 7003702, GB-A 1354507, DE-A 2154370.

As from the middle of the 1970's, research was directed to obtain a more catalyst-efficient telomerization process. In view of this desire, which was in part due to the relatively high costs of the catalyst used in the telomerization process, it was considered essential that after the telomerization reaction the catalyst is obtained (directly or indirectly) in an active form and then reused in the process. In most of the cases, however, the catalyst and the desired reaction products could not be easily recovered from the reaction mixture by means of separation techniques, such as e.g. distillation, precipitation or extraction. Extraction had the disadvantage that both the catalyst and reaction products were soluble in the organic solvents used for extraction. Distillation in general resulted in the catalyst remaining in the reaction by-products which were too heavy to be removed by distillation. Moreover, when distilling off the desired reaction products and/or the heavy by-products, special care should be exercised in view of the low heat stability of the catalyst, leading to catalyst decomposition or metallization at too high distillation temperatures, which would require regeneration of the catalyst.

As the catalyst generally is dissolved in the reaction solution, the residual reaction solution obtained after distillation has been reused or, alternatively, the catalyst was recovered in metallic form by precipitating it from the reaction solution, optionally after removing reaction products and reactants. The former methods however, leads to an increasing amount of residual solution due to by-production of high-boiling matter in repeated use of the solution and also to the problem of treatment of that portion of the catalyst which has lost its activity during the reaction. On the other hand, the latter method has the disadvantage of a complicated operation for reactivating the recovered material.

The following prior art attempted to solve the above discussed problems. U.S. Pat. Nos. 4,142,060 and 4,219,677 describe a telomerization process to prepare 2,7-octadiene derivatives in the presence of a transition metal catalyst, preferably palladium, and a water soluble phosphine, wherein during or after the reaction water is introduced. The water phase obtained at the end of the process contains the water soluble phosphine and the transition metal catalyst. In this way the active transition metal catalyst may be recovered and reused in the process, thus obtaining a continuous process.

U.S. Pat. No. 4,146,738 describes a process for telomerizing a conjugated diene and an alkanol wherein prior to the telomerization tetrakis(triphenyl phosphine) palladium is oxidized with oxygen to partially remove the triphenyl phosphine ligands. The telomerization is then carried out in the presence of this partially oxidized catalyst system. Thereafter, the tetrakis(triphenyl phosphine) palladium is regenerated by adding appropriate amounts of the phosphine and simultaneously distilling the telomerization product from the reaction mixture, thus recovering the tetrakis(triphenyl phosphine) palladium catalyst precursor which is reused in the process as described above.

U.S. Pat. No. 4,196,135 describes a special catalyst, bis[tri(orthototyl) phosphine] palladium for the telomerization of 1,3-dienes. When after the reaction the telomerization product is distilled off at a temperature of lower than 150° C. the particular catalyst complex is precipitated in the form of a solid. The catalyst can then be separated while maintaining its activity and can be immediately put to reuse.

U.S. Pat. Nos. 4,356,333 and 4,417,079 describe a process for preparing n-octadienol by reacting butadiene with water in an aqueous sulfolane solution containing (bi)carbonate ions in the presence of a palladium catalyst, a monodentate phosphine of particular structure and a monodentate tertiary amine. In a next step the reaction mixture is extracted with a hydrocarbon and in a final step at least part of the extraction residue containing the active catalyst components is recycled to the telomerization reaction step. This process sequence is repeated in the examples up to thirty-two times.

EP-A-218100 describes two different methods for the telomerization of a conjugated alkadiene with an organic hydroxy compound to produce an organo-oxyalkadiene. The first method comprises employing the organic hydroxy compound in an amount in excess of the amount stoichiometrically required, in the presence of a palladium catalyst and a phosphorous or antimony ligand, the reaction being conducted in the substantial absence of oxygen and in the presence of a high boiling organic solvent having a boiling point higher than that of the organo-oxyalkadiene. The organo-oxyalkadiene is then separated from the catalyst and the latter recycled for further telomerization. The second method comprises reacting the reactants in the presence of a palladium catalyst and a ligand carrying a hydrophilic group. The reaction is conducted in the substantial absence of oxygen and water and in the presence of a polar solvent to obtain a telomer, said telomer being extracted with a hydrocarbon solvent.

In summary, many attempts have been made to develop a catalyst-efficient continuous telomerization process. These attempts were all directed to recover and recycle the catalyst, which was used in relatively high concentrations, as often as possible.

The object of the present invention is to provide a catalyst-efficient continuous telomerization process which does not require recycling of the catalyst.

Accordingly the present invention provides a continuous process for the telomerization of conjugated dienes comprising reacting a conjugated diene with a compound containing an active hydrogen atom in the liquid phase in the presence of a Group VIII transition metal catalyst and a tertiary phosphorous, arsenic or antimony ligand compound, characterized in that at least 10,000 moles of conjugated diene are fed to the reaction zone per gram atom of the Group VIII transition metal of the catalyst fed to the reaction zone.

Surprisingly, it has been discovered that by using a high ratio between the conjugated diene fed to the reaction zone and the Group VIII transition metal catalyst fed to the reaction zone, expressed in moles of diene per gram atom of Group VIII transition metal present in the catalyst (hereinafter referred to as "diene/catalyst ratio"), it is no longer required, in order to come to a catalyst-efficient continuous telomerization process, to recover the catalyst after the telomerization reaction step or zone in an active form and recycle it. In this way a favorable catalyst single pass or once through process may be obtained.

Another great advantage is that in a recovery step or zone which follows the reaction step or zone, the recovery of the desired reaction products can be optimized without having to consider conditions for keeping the catalyst in a form which can be recycled.

The conjugated diene employed as reactant in the process of the invention comprises 1,3-butadiene and its 2- and/or 3-substituted derivatives or mixtures thereof. Exemplary of suitable substituents are alkyl and halogen substituents. Preferred alkyl moieties are lower alkyl, with methyl being particularly preferred. A preferred halogen substituent is chlorine. Suitable examples of conjugated dienes include 1,3-butadiene, isoprene, piperylene, 2,3-dimethyl-1,3-butadiene, chloroprene and the like.

In the process of the present invention preferably 1,3-butadiene is used. The 1,3-butadiene may be employed as pure butadiene or as a crude C₄-hydrocarbons mixture. Such a crude C₄-mixture contains, besides 1,3-butadiene, other C₄-hydrocarbons such as butenes and butanes. These other C₄-hydrocarbons do not essentially influence conversion of the 1,3-butadiene and selectivity towards the desired telomerization product. Such a crude C₄-hydrocarbon mixture can be produced as a by-product in the pyrolysis of naphtha, gas oil, LPG et cetera. As the selectivity and conversion towards the desired telomerization product, based on the 1,3-butadiene present in the crude C₄-hydrocarbons mixtures are about the same as for pure 1,3-butadiene, it is advantageous to use the crude C₄-mixture in the present process since doing so avoids the investments and costs associated with first extracting and purifying the 1,3-butadiene from the crude C₄-mixture, which is one of the primary sources of 1,3-butadiene. The crude C₄-mixture produced in the cracking of naphtha, gas oil or LPG usually has a 1,3-butadiene content of 20 to 70% by weight. When the crude C₄-mixture contains acetylenes, it is advantageous to selectively hydrogenate the crude C₄-mixture in order to remove these acetylenes prior to its use in the present process.

The compound containing an active hydrogen atom employed as co-reactant in the process of the invention can be any compound containing at least one reactive hydrogen atom. Suitable examples include alcohols, hydroxy-aromatic compounds, carboxylic acids, ammonia, primary and secondary amines, compounds containing reactive methylene groups, silanols and water. In case a compound containing more than one reactive hydrogen atom is used, a product may be formed in which all of those reactive hydrogen atoms are replaced by an oligomerized, and especially dimerized conjugated diene unit.

Exemplary of such alcohols are mono- or polyhydric alcohols containing primary OH-groups and which can be linear or branched saturated compounds having up to 20 carbon atoms, as well as unsaturated alcohols such as allylalcohol; especially the up to 8 carbon atoms, such as methanol, ethanol, propanol, butanol, ethylene glycol, propylene glycol, glycerol and the like. Preferably a primary aliphatic alcohol or a hydroxy aromatic compound is used, more preferably methanol or ethanol. Secondary alcohols like iscopropanol and the cycloaliphatic alcohols such as cyclopentanol and cyclohexanol may also be used advantageously.

Exemplary of hydroxy-aromatic compounds are aromatic compounds containing one or more rings such as phenol, benzylalcohol, cresols, xylenols, naphtol, as well as polyhydric compounds such as resorcinol, hydroquinone and pyrocatechol. Also alkyl-, alkoxy- and/or halogen-substituted aromatic hydroxy compounds may be used, such as o-methoxy phenol, p-chloro phenol and the like.

Suitable examples of carboxylic acids include aliphatic carboxylic acids with up to about 20 carbon atoms. Preferred carboxylic acids are those having 1-6 carbon atoms such as, e.g. acetic acid, propionic acid, and butyric acid. Examples of suitable aromatic carboxylic acids include benzoic acid and toluene carboxylic acid. Representative examples of dibasic acids are adipic acid, the phthalic acids and the like.

Exemplary of suitable amine compounds are ammonia and primary and secondary amines. Suitable amine compounds include for example primary aliphatic amines, such as methyl amine, ethyl amine, butyl amine, dodecyl amine and the like; primary aromatic amines, such as aniline, toluidine, benzyl amine and the like; secondary amines such as dimethyl amine, diethyl amine, N-methyl aniline, dicyclohexyl amine, methyl hexyl amine, and the like; as well as polyamines such as phenylene diamine, ethylene diamine; and heterocyclic amines, such as piperidine, pyridine and the like.

Suitable examples of compounds containing reactive methylene groups include acetyl acetone, benzoyl acetone, esters of acetyl acetic acid, such as ethyl acetyl acetate, diethyl maleate, and nitrated compounds such as nitromethane.

As co-reactant in the process of the present invention also water may be used. This results in the production of an unsaturated alcohol. Water as co-reactant requires the use of a solvent in order to secure a homogeneous reaction mixture, as water and the conjugated diene normally do not mix.

The preferred telomerization product of the present process is a 1-alkoxy or aryloxy substituted 2,7-alkadiene, and more preferably 1-methoxy-2,7-octadiene resulting from the telomerization reaction between methanol and 1,3-butadiene.

In general the ratio between the compound containing an active hydrogen atom and the conjugated diene (hereinafter referred to as "reactant ratio" and expressed in moles of compound containing an active hydrogen atom fed to the reaction zone per mole of conjugated diene fed to the reaction zone) is higher than 0.5. According to the present invention the compound containing an active hydrogen atom is fed to the reaction zone in a relative amount of preferably 1 to 20 moles, and more preferably 1 to 10 moles per mole of conjugated diene.

The catalyst to be used in the process of the present invention can be any catalyst which, when the reactants are contacted in its presence under suitable reaction conditions, promotes the formation of an oligomer, and especially dimer, of the conjugated diene under concomitant addition at its terminal position of the compound containing an active hydrogen atom. Examples of telomerization catalysts are the transition metals Fe, Co, Ni, Ru, Rh, Pd, Os, Ir and Pt (hereinafter referred to as "Group VIII transition metals") and compounds thereof, including those supported on an inert carrier. Suitable examples of such catalysts for use in the process of the present invention are described in an article of A. Behr titled "Homogeneous Transition Metal Catalysts" in Aspects of Homogeneous Catalysis (1984), Vol. 5, pages 3-73. It is preferred that the catalyst is homogeneous under reaction conditions.

Preferably a nickel, rhodium, palladium or platinum catalyst is used as the Group VIII transition metal catalyst, more preferably a palladium catalyst. Both palladium(II) compounds and palladium(O) complexes may be used in the present process. Examples of suitable palladium(II) compounds include: palladium(II) salts, such as palladium bromide, palladium chloride, palladium formate, palladium acetate, palladium propionate, palladium octanoate, palladium carbonate, palladium sulfate, palladium nitrate, palladium borate, palladium citrate, palladium hydroxide, palladium aryl-or alkylsulfonates, sodium-or potassium chloropalladate; compounds of formula $PdX_2L_2$ in which X is a monovalent acid residue and L is a ligand selected from the group of organic nitriles, such as benzonitrile, tertiary amines, e.g. pyridine, quinoline, picoline, lutidine and triethylamine, an example of such a $PdX_2L_2$ compound being dichlorobis(benzonitrile) palladium; palladium chelates such as palladium acetylacetonate; n-allyl complexes, like n-allyl palladium chloride or acetate, and bis(n-allyl) palladium; and 1,5-cyclooctadiene palladium chloride. It is noted that in case a palladium halide is used, also a catalyst activator is required, in order to dissociate the palladium halide in the solution so as to form a catalytically active species. Suitable palladium(O) complexes include a wide variety of ligands, such as phosphines, alkenes, dienes, nitriles. Examples of these include tetrakis(triphenyl phosphine) palladium, bis(1,5-cyclooctadiene) palladium, and the like.

In the process of the present invention preferably a divalent palladium compound is used as catalyst, and more preferably palladium(II) acetylacetonate. This palladium salt is readily available, relatively inexpensive and gives excellent results.

Besides the Group VIII transition metal catalyst there is also employed in the process of the present invention a tertiary phosphorous, arsenic or antimony ligand compound. Suitable ligand compounds comprise the substituted hydrides of phosphorous, arsenic or antimony and especially those in which the hydride is fully substituted by alkyl, alkoxy, cycloalkyl, aryl and-/or aryloxy groups. Also ligand compounds in which two phosphorous, arsenic or antimony atoms, respectively, are attached to each other through an alkylene group can also be used. Examples of the latter compounds include diphosphines, diarsines and distibines.

Tertiary phosphines which may be used advantageously include phosphines containing (cyclo)alkyl and/or aryl groups. Examples of suitable trialkyl phosphines are triethyl phosphine, tri-n-butyl phosphine, tri-isobutyl phosphine, tripentyl phosphine, trihexyl phosphine, trioctyl phosphine, trilauryl phosphine, lauryl dimethyl phosphine, hexyl dipropyl phosphine and ethyl butyl octyl phosphine. Examples of suitable phosphines containing one or more aromatic groups or cycloalkyl groups are tricyclohexyl phosphine, triphenyl phosphine, tri(p-tolyl) phosphine, dimethyl phenyl phosphine, methyl diphenyl phosphine, tri(m-ethylphenyl) phosphine and tri(2,4-dimethyl phenyl) phosphine. A suitable diphosphine which may be used is bis(diphenyl phosphine)-ethane. Also the arsine and antimony homologs may be advantageously used. The above-mentioned ligand compounds may further be substituted by halogen atoms, such as chlorine atoms, nitrile and/or nitro groups and the like. Also ligand compounds which contain in addition hydrophilic groups, such as $-COOM$, $-SO_3M$, and/or $-NH_2$ groups attached directly or via an alkylene group to the phosphine substituent(s), may be used. In the above-mentioned groups M represents an inorganic or organic cationic residue, such as an alkali or alkaline earth metal cation, a quaternary ammonium ion or the like. In particular ligand compounds containing hydrophilic substituents are used when water is used as co-reactant.

When a mono or multivalent Group VIII transition metal compound, such as a divalent palladium compound is used as the catalyst, it may be reduced by the conjugated diene present in the reaction system. The active species appear not to be formed instantaneously, but they take a certain period of time to be formed, which time period is referred to as the induction period. It has been found that by adding a compound having basic properties (hereinafter referred to as "catalyst promoter") the induction period is surprisingly diminished to substantially zero.

Suitable catalyst promoters include alkali metal, alkaline earth metal or quaternary ammonium hydroxides, alcoholates or alkoxides, enolates, phenoxides, alkali metal borohydride, hydrazines and the like. As catalyst promoter preferably the alkali metal salt, especially the sodium or potassium salt of the compound containing an active hydrogen atom is used. These alkali metal salts, for examples may be added as such or may be formed in situ by dissolving an alkali metal in the compound containing an active hydrogen atom.

The ligand compound is generally fed to the reaction zone in a relative amount of 1 to 20 moles, and preferably 2 to 15 moles of ligand compound per gram atom of the Group VIII transition metal of the catalyst. The ligand compound may be added as separate compound to the reaction mixture or zone or to the catalyst make-up solution, or it may be incorporated in a Group VIII transition metal catalyst complex. When, for example, tetrakis(triphenyl phosphine) palladium is used as catalyst compound, it is generally not necessary to add additional triphenyl phosphine as ligand compound.

The catalyst promoter is usually employed in an amount which is at least approximately stoichiometric to the amount of catalyst employed. Preferably the catalyst promoter is fed to the reaction zone in a relative amount of at least 0.5. more preferably at least 1, to not more than 1,000 moles, and more preferably not more than 150 moles of promoter per gram atom of the Group VIII transition metal catalyst.

In the present process at least 10,000 moles of conjugated diene are fed to the reaction zone per gram atom of the Group VIII transition metal of the catalyst fed to the reaction zone. Preferably at least 20,000 moles and more preferably at least 50,000 moles of conjugated diene are fed per gram atom of the Group VIII transition metal of the catalyst. The upper limit of the diene/catalyst ratio is not critical, and can be as high as 1,000,000.

It has been found advantageous to feed conjugated diene to the reaction zone at more than one point along the reaction zone. By feeding a first stream of the conjugated diene to the beginning of the reaction zone and one or more further streams downstream of this point, a high diene/catalyst ratio can be maintained over a substantial portion of the reaction zone, which has a beneficial influence on the reaction rate.

The process of the present invention may be conducted in the presence or absence of a solvent which is capable of dissolving the reactants and catalyst and is inert to the reactants and the products prepared therefrom. When one or more of the reactants are not liquid under reaction conditions or if the reactants are poorly miscible or substantially immiscible with each other (e.g. water and 1,3-butadiene) then preferably a solvent is used to secure the desired homogeneous system. Any solvent that will solubilize the conjugated diene, the compound containing an active hydrogen atom and the catalyst, ligand and optional promoter components may be used in the present process. Suitable inert solvents are (cyclo)alkanes, for example $C_{6-12}$-alkanes and cyclohexane or a mixture thereof; aromatic compounds, e.g. benzene, toluene, xylene, naphthenes; a polar solvent, such as tertiary alcohols, an amide, e.g. acetamide, dimethyl acetamide or dimethyl formamide; a nitrile compound, such as acetonitrile or benzonitrile; a ketone, e.g. acetone or methyl ethyl ketone; an ester compound, such as ethylene glycol diacetate; an ether compound, e.g. ethyl ether, propyl ether, dioxane, tetrahydrofuran, and anisole, or a lower alkyl-disubstituted ether of mono- or diethylene glycol; and dimethylsulfoxide and sulfolane. Also in some cases water may be used as solvent.

The process according to the present invention is preferably conducted in the substantial absence of oxygen, as oxygen reacts with the ligand compound and consequently results in decreased catalyst activity.

The temperature at which the process of the present invention is carried out is not critical. Normally, temperatures between ambient temperature and 150° C. can be used. Preferably, the reaction temperature is 50°-1000° C. and more preferably 70°-100° C.

The pressure at which the telomerization reaction is carried out is not critical provided it is sufficient to maintain the reaction mixture in the liquid state. Generally the reaction pressure lies between 1 and 40 bars, preferably between 5 and 30 bars and most preferably between 10 and 20 bars.

In view of the very low catalyst concentrations used in the process of the present invention, the reaction mixture should be allowed sufficient time to react. It has been found that the catalyst remains active even after a long residence time in the reaction zone, provided a large excess of conjugated diene is present. Generally, residence times of from 0.1 to 100 hours give good results, depending on reaction temperatures, reactants, catalyst system and optional solvent. Preferably residence times lie between 0.1 and 20 hours and more preferably between 0.2 and 10 hours.

As reaction unit any type of continuous reactor unit may be used. Examples of suitable reactors include a continuously stirred tank reactor and a tubular reactor. In the process according to the present invention it is preferred to carry out the telomerization reaction in a tubular reactor, and more preferably the reaction is carried out in a tubular reactor with plug flow.

As mentioned hereinbefore, in the product and catalyst recovery step of the process attention can be focused primarily on the product recovery. This means that the telomerization product can be isolated by means of any suitable method without having to consider keeping the catalyst in an active or recuperable form. It goes of course without saying, that as much catalyst as possible is removed from the process stream. After the catalyst is removed it may be regenerated, discarded or used for some other purpose. So according to the present invention a high catalyst efficiency may be obtained without having to recycle the catalyst in an active form, i.e. in a catalyst once through or single pass process, whereas the prior art processes require recovery of the active catalyst and reuse of it on a continuous basis.

Depending on the physical properties of reactants, catalyst components, optional solvent and desired telomerization product, the desired product may be isolated by subjecting the reaction mixture to one or more distillation, extraction, or other well known separation techniques, or a combination thereof. In case of distillation, the catalyst generally remains in the distillation residue. It may be separated from the residue by precipitation or filtration or any other suitable known method. The unconverted reactants are generally separated by means of distillation techniques and reused in the telomerization process.

In case a crude $C_4$-hydrocarbons mixture is used then the telomerization reaction is carried out in such a manner that as much of the 1,3-butadiene present in the crude $C_4$-hydrocarbons mixture is converted, because recycle of the used crude $C_4$-hydrocarbons mixture would lead to build-up of unreactive butenes and butanes in the reaction mixture.

Although in the process of the present invention the relative amounts of reactants and catalyst components are expressed as amounts fed to the reaction zone, it will be clear that not all of the reactants and catalyst components need to be introduced into the reaction zone as separate streams. For example, one or more of the catalyst components may be added to the stream of the compound having an active hydrogen atom, and this combined stream may then be added to the reaction zone. Other embodiments may also be used without deviating from the spirit of the present invention.

The telomerization products produced according to the present invention are useful intermediates for a variety of applications, such as e.g. in the preparation of surfactants, herbicides, saturated ethers, alcohols, acids, esters, herbicides, etcetera. In particular, the telomerization products produced from 1,3-butadiene are valuable intermediates in the production of 1-octene, by subjecting said products first to a hydrogenation reaction to give a 1-substituted octane, which subsequently is decomposed to give 1-octene.

The process according to the present invention is further illustrated by means of the following examples which show different embodiments of the present process, though are not intended to limit the scope of the invention.

INTRODUCTION TO EXAMPLES

In the following experiments a tubular reactor with plug-flow is used to carry out the process according to the present invention. The plug-flow reactor is provided with a jacket in order to control the temperature in the reactor by means of water flowing through the jacket. The conjugated diene, the compound containing an active hydrogen atom and the catalyst solution are fed to the reactor. During all the experiments the reaction pressure is maintained at 14 bar in order to maintain all reactants in the liquid phase.

The catalyst solutions used in the experiments are prepared as follows.

Catalyst solution A is prepared by dissolving 60 g of palladium acetylacetonate (0.2 moles) and 103 g of triphenyl phosphine (0.4 moles) in 18 l of deoxygenated methanol; resulting in a Pd concentration of 11 mmole/l. The ligand/catalyst ratio is 2.

Catalyst solution B is prepared by dissolving 18 g of palladium acetylacetonate (59 mmole) and 31 g triphenyl phosphine (118 mmole) in 16 l of deoxygenated methanol; resulting in a Pd concentration of 3.7 mmole/l. The ligand/catalyst ratio is 2.

In the Examples below conversion (expressed in moles of conjugated diene converted/moles of conjugated diene fed $\times$ 100%), selectivity towards telomerization products (expressed as moles of conjugated diene converted to the telomerization product/total moles of conjugated diene converted $\times$ 100%) and catalyst efficiency (expressed as grams of desired product/gram of catalyst transition metal used) are specified for different residence times in the plug flow reactor. This was done by taking samples of the reaction mixture along the plug-flow reactor and analyzing these samples by gas chromatography.

In these Examples below,
MOD-1 is 1-methoxy-2,7-octadiene (desired product),
MOD-3 is 3-methoxy-1,7-octadiene, and
OT is 1,3,7-octatriene.

EXAMPLE 1

As described in the introductory section hereinbefore 1.6 kg/h of deoxygenated methanol, 1.3 kg/h of 1,3-butadiene and 5 g/h of catalyst solution A are fed into the plug-flow reactor. The temperature in the reactor is maintained at 90° C. This results in the following concentrations at the reactor inlet: 12.3 mole/l of methanol, 5.7 mole/l of 1,3-butadiene, 16.4 μmole/l of Pd. The initial 1,3-butadiene/Pd ratio is 350,000 mole/gram atom, and the initial methanol/1,3-butadiene ratio is 2 mole/mole.

The results are summarized in Table 1.

TABLE 1

| Residence time [h] | Conversion [%] | Selectivity [%] | | | Catalyst efficiency [g MOD-1/ g Pd] |
|---|---|---|---|---|---|
| | | MOD-1 | MOD-3 | OT | |
| 0.6 | 5.6 | 87.6 | 5.0 | 7.4 | 11,400 |
| 1.2 | 12.9 | 84.9 | 5.3 | 9.8 | 25,400 |
| 1.9 | 20.2 | 85.0 | 5.3 | 9.7 | 39,800 |
| 2.5 | 25.3 | 84.4 | 5.4 | 10.2 | 49,500 |

EXAMPLE 2

In the same manner as described in Example 1 0.9 kg/h of deoxygenated methanol, 1.2 kg/h of a crude C$_4$-hydrocarbons mixture and 45 g/h of catalyst solution B are fed into the reactor, which is maintained at a temperature of 80° C. Analysis of the crude C$_4$-hydrocarbons mixture shows the following composition: 7 wt % of butanes, 20.0 wt % of isobutene, 24.6 wt % of n-butenes, 47.9 wt % of 1,3-butadiene and less than 60 ppm of total acetylenes. This results in the following initial concentrations: 9.2 mole/l of methanol, 3.0 mole/l of 1,3-butadiene, 62.6 μmole/l of Pd. The initial 1,3-butadiene/Pd ratio is 50,000 mole/gram atom, and the initial methanol/1,3-butadiene ratio is 3 mole/mole.

The results are summarized in Table 2.

TABLE 2

| Residence time [h] | Conversion [%] | Selectivity [%] | | | Catalyst efficiency [g MOD-1/ g Pd] |
|---|---|---|---|---|---|
| | | MOD-1 | MOD-3 | OT | |
| 0.1 | 2.5 | 85.0 | 4.7 | 10.3 | 700 |
| 0.9 | 25.0 | 83.3 | 5.7 | 11.1 | 6,900 |
| 2.5 | 53.3 | 82.4 | 5.7 | 12.0 | 14,600 |
| 3.3 | 62.3 | 82.5 | 5.6 | 12.0 | 17,100 |

EXAMPLE 3

In the same manner as described in Example 1 1.3 kg/h of deoxygenated methanol, 0.8 kg/h of 1,3-butadiene and 45 g/h of catalyst solution B are fed into the reactor, which is maintained at a temperature of 80° C. This results in the following initial concentrations: 13.2 mole/l of methanol, 4.6 mole/l of 1,3-butadiene and 67.3 μmole/l of Pd. The initial 1,3-butadiene/Pd radio is 68,000 mole/gram atom, and the initial methanol/1,3-butadiene ration is 3 mole/mole.

The results are summarized in Table 3.

TABLE 3

| Residence time [h] | Conversion [%] | Selectivity [%] | | | Catalyst efficiency [g MOD-1/ g Pd] |
|---|---|---|---|---|---|
| | | MOD-1 | MOD-3 | OT | |
| 0.2 | 0.4 | 94.9 | 5.1 | 0 | 200 |
| 1.0 | 18.4 | 89.9 | 4.7 | 5.3 | 7,600 |
| 1.8 | 39.4 | 90.6 | 4.9 | 4.6 | 16,500 |
| 2.6 | 62.5 | 90.3 | 5.0 | 4.7 | 26,100 |
| 3.5 | 74.8 | 90.5 | 5.1 | 4.4 | 31,400 |

EXAMPLE 4

Example 3 is repeated except that in addition also 30 g/h of a catalyst promoter solution is fed to the reactor. The promoter solution is a 1.5 wt % solution of sodium methoxide in deoxygenated methanol. The initial concentrations are: 13.4 mole/l of methanol, 4.5 mole/l of 1,3-butadiene and 66.5 μmole/l of Pd. The 1,3-butadiene/Pd ratio and methanol/1,3-butadiene ratio are the same as in Example 3. The sodium methoxide/Pd ratio is 100 mole/gram atom. The results are summarized in Table 4.

TABLE 4

| Residence time [h] | Conversion [%] | Selectivity [%] | | | Catalyst efficiency [g MOD-1/ g Pd] |
|---|---|---|---|---|---|
| | | MOD-1 | MOD-3 | OT | |
| 0.2 | 13.1 | 88.0 | 5.9 | 6.1 | 5,300 |
| 1.0 | 62.7 | 89.7 | 5.4 | 4.9 | 26,000 |
| 1.8 | 82.8 | 89.5 | 5.5 | 5.0 | 34,400 |
| 2.6 | 92.6 | 89.4 | 5.6 | 5.0 | 38,400 |
| 3.5 | 95.7 | 89.4 | 5.6 | 5.0 | 39,700 |

This Example 4 shows the beneficial effect of the catalyst promoter compared to the reaction system without said catalyst promoter.

EXAMPLE 5

2.5 kg/h of deoxygenated methanol, 0,7 kg/h of 1,3-butadiene and 60 g/h of catalyst solution A are fed into the plug-flow reactor which is maintained at a temperature of 90° C. The initial concentrations are: 18.2 mole/l of methanol, 3.0 mole/l of 1,3-butadiene and 194.4 μmole/l of Pd. The initial 1,3-butadiene/Pd ratio is 15,000 mole/gram atom and the initial methanol/1,3-butadiene ratio is 6 mole/mole. In a separate experiment (Example 5A), an additional flow of 0.4 kg/h of 1,3-butadiene is injected half way through the reactor.

The results are summarized in Table 5.

TABLE 5

| Residence time [h] | Conversion [%] | Selectivity [%] | | | Catalyst efficency [g MOD 1/ g Pd] |
|---|---|---|---|---|---|
| | | MOD-1 | MOD-3 | OT | |
| Without extra addition: Example 5 | | | | | |
| 1.2 | 79 | 88.0 | 5.9 | 6.1 | 7,200 |
| 2.4 | 90 | 88.7 | 5.1 | 6.2 | 8,300 |
| With extra addition: Example 5A | | | | | |
| 2.1 | 88 | 86.1 | 6.0 | 7.3 | 12,400 |

This Example shows the beneficial effect of a multiple 1,3-butadiene injection.

We claim:

1. Continuous process for the telomerization of conjugated dienes comprising reacting in a reaction zone a conjugated diene with a compound containing an active hydrogen atom in the liquid phase in the presence of a Group VIII transition metal catalyst, a ligand compound selected from the group of tertiary phosphorous, tertiary arsenic and tertiary antimony compounds, and a catalyst promoter compound having basic properties, wherein at least 10,000 moles of conjugated diene are fed to the reaction zone per gram atom of the Group VIII transition metal of the catalyst fed to the reaction zone and the catalyst is not recycled.

2. Process according to claim 1 wherein the conjugated diene is 1,3-butadiene.

3. Process according to claim 2 wherein a crude $C_4$-hydrocarbon mixture containing 1,3-butadiene is used.

4. Process according to claim 1 wherein the compound containing an active hydrogen atom is a primary aliphatic alcohol or an aromatic hydroxy compound.

5. Process according to claim 4 wherein the primary aliphatic alcohol is methanol or ethanol.

6. Process according to claim 1 wherein 1-methoxy-2,7-octadiene is a product prepared from the telomerization process.

7. Process according to claim 1 wherein the compound containing an active hydrogen atom is fed to the reaction zone in a relative amount of 1 to 20 moles per mole of conjugated diene.

8. Process according to claim 1 wherein the Group VIII transition metal catalyst is a palladium catalyst.

9. Process according to claim 1 wherein the ligand compound is a tertiary phosphine containing (cyclo)alkyl and/or aryl groups.

10. Process according to claim 1 wherein the ligand compound is fed to the reaction zone in a relative amount of 1 to 20 moles per gram atom of the Group VIII transition metal of the catalyst.

11. Process according to claim 1 wherein the catalyst promoter is an alkali metal salt of the compound containing an active hydrogen atom.

12. Process according to claim 1 wherein the catalyst promoter is fed to the reaction zone in a relative amount of 1 to 1,000 moles of promoter per gram atom of the Group VIII transition metal catalyst.

13. Process according to claim 1 wherein at least 20,000 moles of conjugated diene are fed to the reaction zone per gram atom of the Group VIII transition metal of the catalyst fed to the reaction zone.

14. Process according to claim 1 wherein conjugated diene is fed to the reaction zone at more than one point along the reaction zone.

15. Process according to claim 1 wherein the telomerization process is carried out at a temperature of about 50°–100° C.

16. Continuous process for the telomerization of conjugated dienes comprising reacting in a reaction zone a conjugated diene with a compound containing an active hydrogen atom in the liquid phase in the presence of a palladium catalyst, in the presence of a tertiary phosphine containing (cyclo)alkyl and/or aryl groups as ligand compound, and in the presence of an alkali metal salt of the compound containing an active hydrogen atom as catalyst promoter, wherein at least 10,000 moles of conjugated diene are fed to the reaction zone per gram atom of the palladium catalyst fed to the reaction zone and the catalyst is not recycled.

17. Continuous process for the telomerization of conjugated dienes comprising reacting in a reaction zone 1,3-butadiene with methanol in the liquid phase in the presence of a palladium catalyst, in the presence of a tertiary phosphine containing (cyclo)alkyl and/or aryl groups as ligand compound, and in the presence of a sodium methoxide catalyst promoter, wherein at least 10,000 moles of 1,3-butadiene are fed to the reaction zone per gram atom of the palladium catalyst fed to the reaction zone and the catalyst is not recycled.

* * * * *